US009526402B2

(12) United States Patent
Honda

(10) Patent No.: US 9,526,402 B2
(45) Date of Patent: Dec. 27, 2016

(54) ENDOSCOPE APPARATUS

(71) Applicant: OLYMPUS CORPORATION, Tokyo (JP)

(72) Inventor: Kazuki Honda, Higashiyamato (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/732,142

(22) Filed: Jun. 5, 2015

(65) Prior Publication Data
US 2015/0265136 A1 Sep. 24, 2015

Related U.S. Application Data

(63) Continuation of application No. PCT/JP2013/082735, filed on Dec. 5, 2013.

(30) Foreign Application Priority Data

Dec. 5, 2012 (JP) .................. 2012-266358

(51) Int. Cl.
A61B 1/06 (2006.01)
A61B 1/04 (2006.01)
A61B 1/00 (2006.01)
A61B 1/05 (2006.01)
G02B 23/24 (2006.01)
(Continued)

(52) U.S. Cl.
CPC ....... *A61B 1/00096* (2013.01); *A61B 1/00091* (2013.01); *A61B 1/00181* (2013.01); *A61B 1/015* (2013.01); *A61B 1/051* (2013.01); *A61B 1/0676* (2013.01); *A61B 1/126* (2013.01); *G02B 23/2423* (2013.01)

(58) Field of Classification Search
USPC ... 600/109–113, 127, 129, 160–181; 348/45, 65–76
See application file for complete search history.

(56) References Cited

U.S. PATENT DOCUMENTS

2004/0158129 A1* 8/2004 Okada ............... A61B 1/00096
600/168
2007/0203396 A1* 8/2007 McCutcheon ..... A61B 1/00082
600/173
(Continued)

FOREIGN PATENT DOCUMENTS

JP S60-53920 A 3/1985
JP 4955838 B2 6/2012
JP 2012-157577 A 8/2012

OTHER PUBLICATIONS

Jan. 7, 2014 International Search Report issued in International Patent Application No. PCT/JP2013/082735.
(Continued)

*Primary Examiner* — Ryan Henderson
(74) *Attorney, Agent, or Firm* — Oliff PLC

(57) ABSTRACT

The endoscope apparatus effects shifting without disappearance of a side observation image until a boundary between the side observation image and a non-image-forming region reaches an end of a light receiving surface so that a displacement of a shift distance K is produced between an optical axis of an imaging optical system and a center position L of the light receiving surface of an imaging section, adjusts a magnification of the imaging optical system, and magnifies and displays a combined image of a front observation image and the side observation image.

6 Claims, 5 Drawing Sheets

(51) Int. Cl.
 *A61B 1/015* (2006.01)
 *A61B 1/12* (2006.01)

(56) References Cited

U.S. PATENT DOCUMENTS

2011/0282155 A1* 11/2011 Kase .................... A61B 1/0615
 600/165
2012/0157773 A1 6/2012 Honda et al.

OTHER PUBLICATIONS

Nov. 4, 2014 Office Action issued in Japanese Application No. 2014-537211.
Jun. 18, 2015 International Preliminary Report on Patentability issued in International Application No. PCT/JP2013/082735.

* cited by examiner

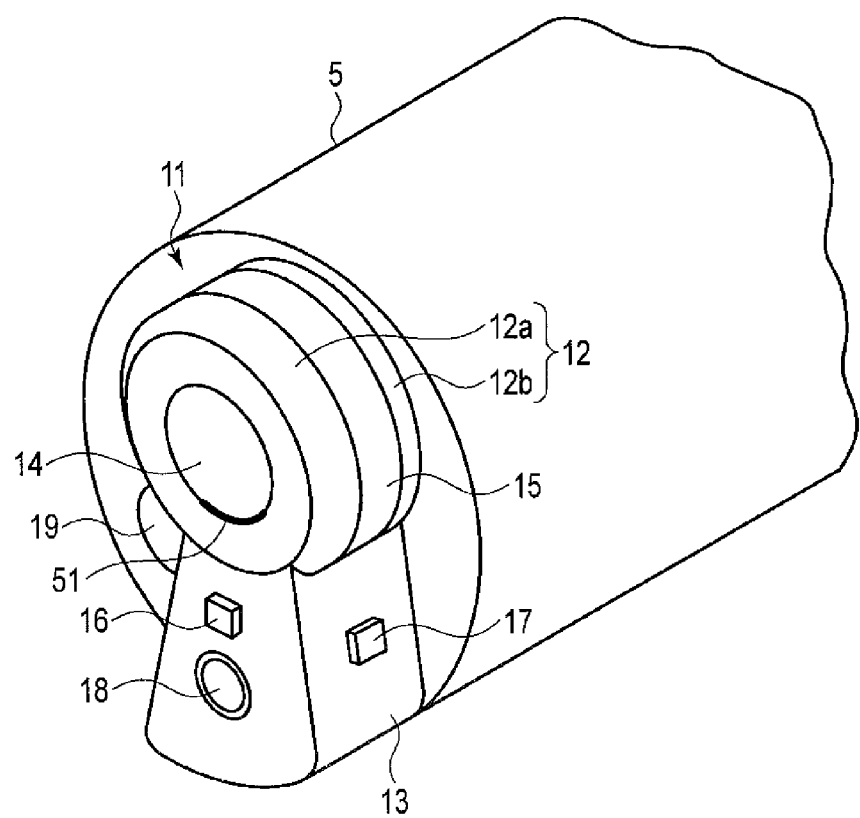
F I G. 2A
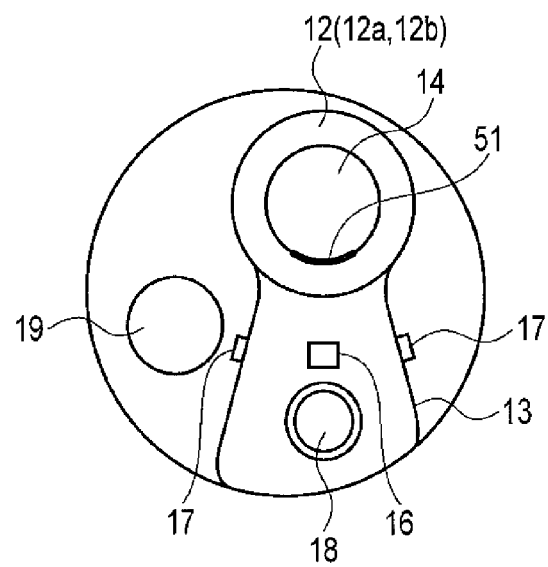
F I G. 2B

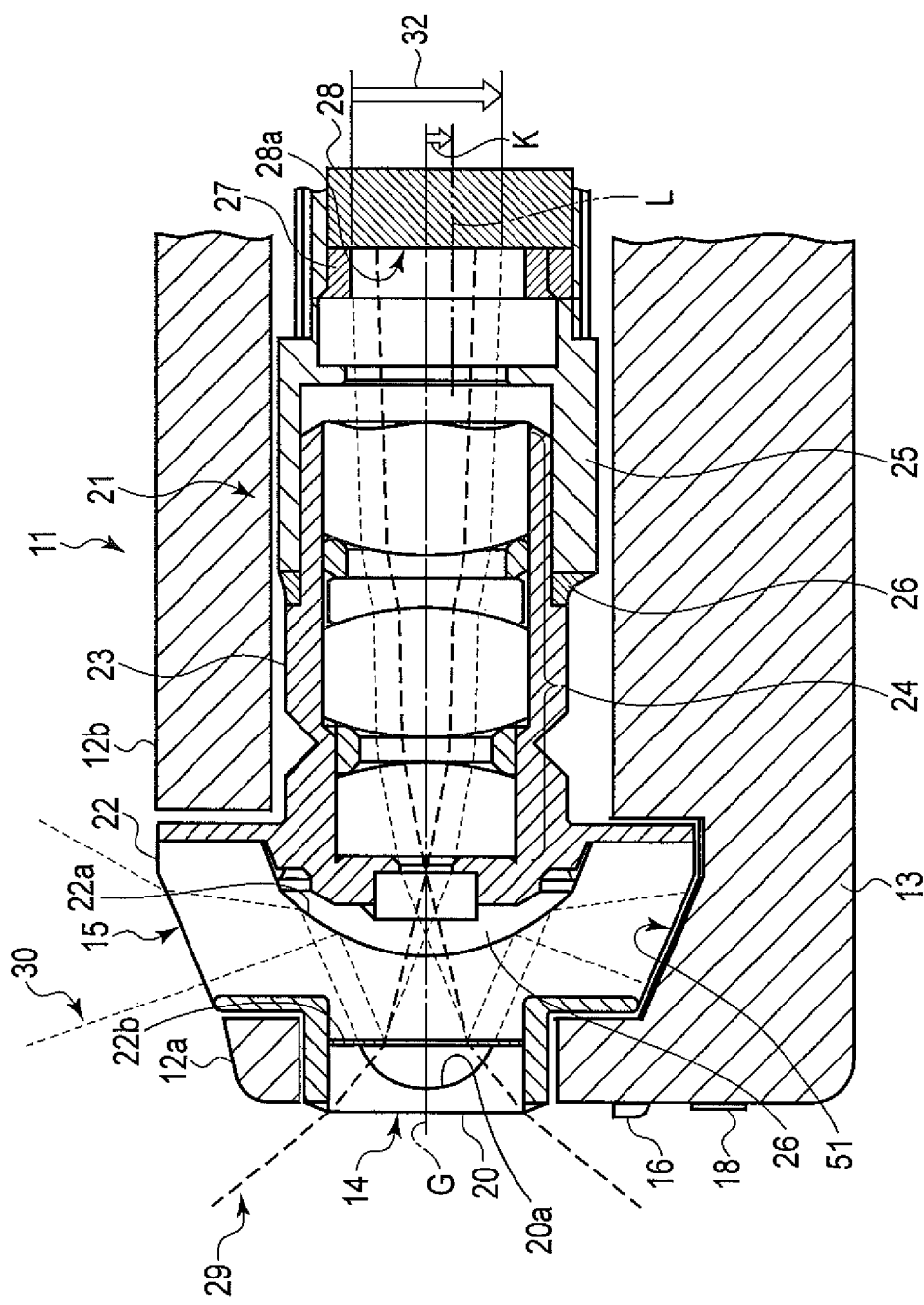
F I G. 3

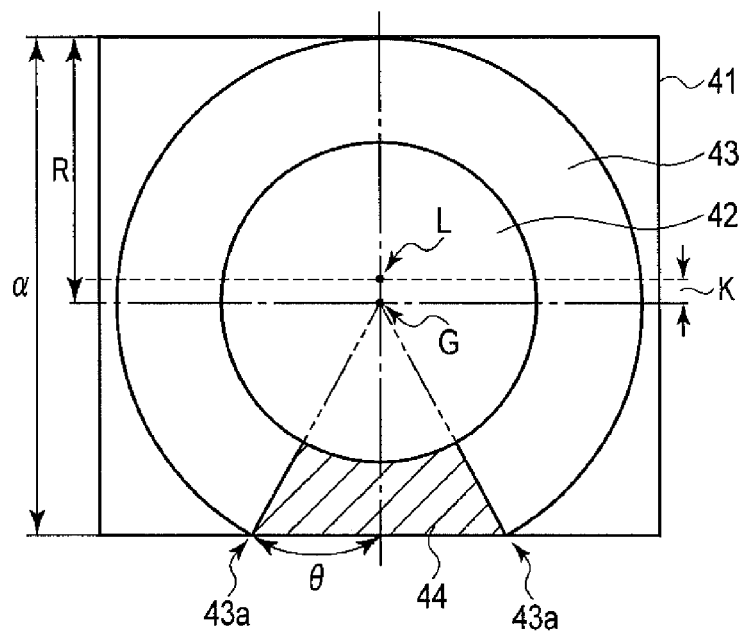
F I G. 4A
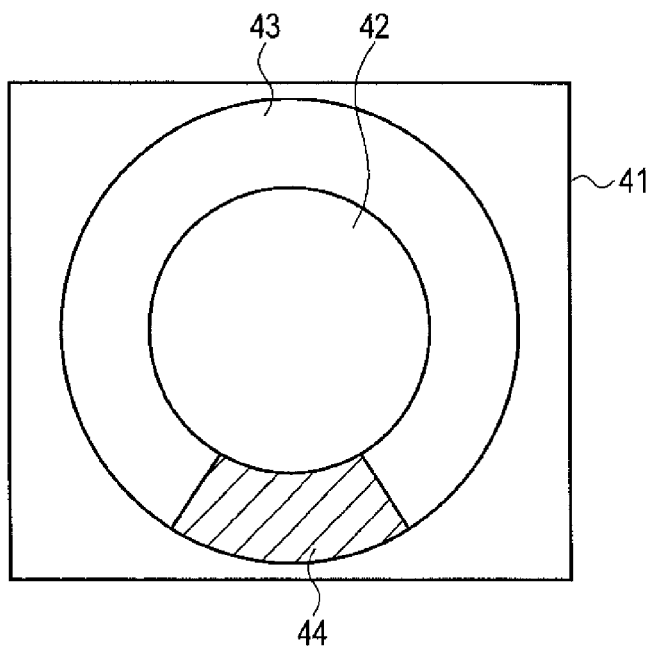
F I G. 4B

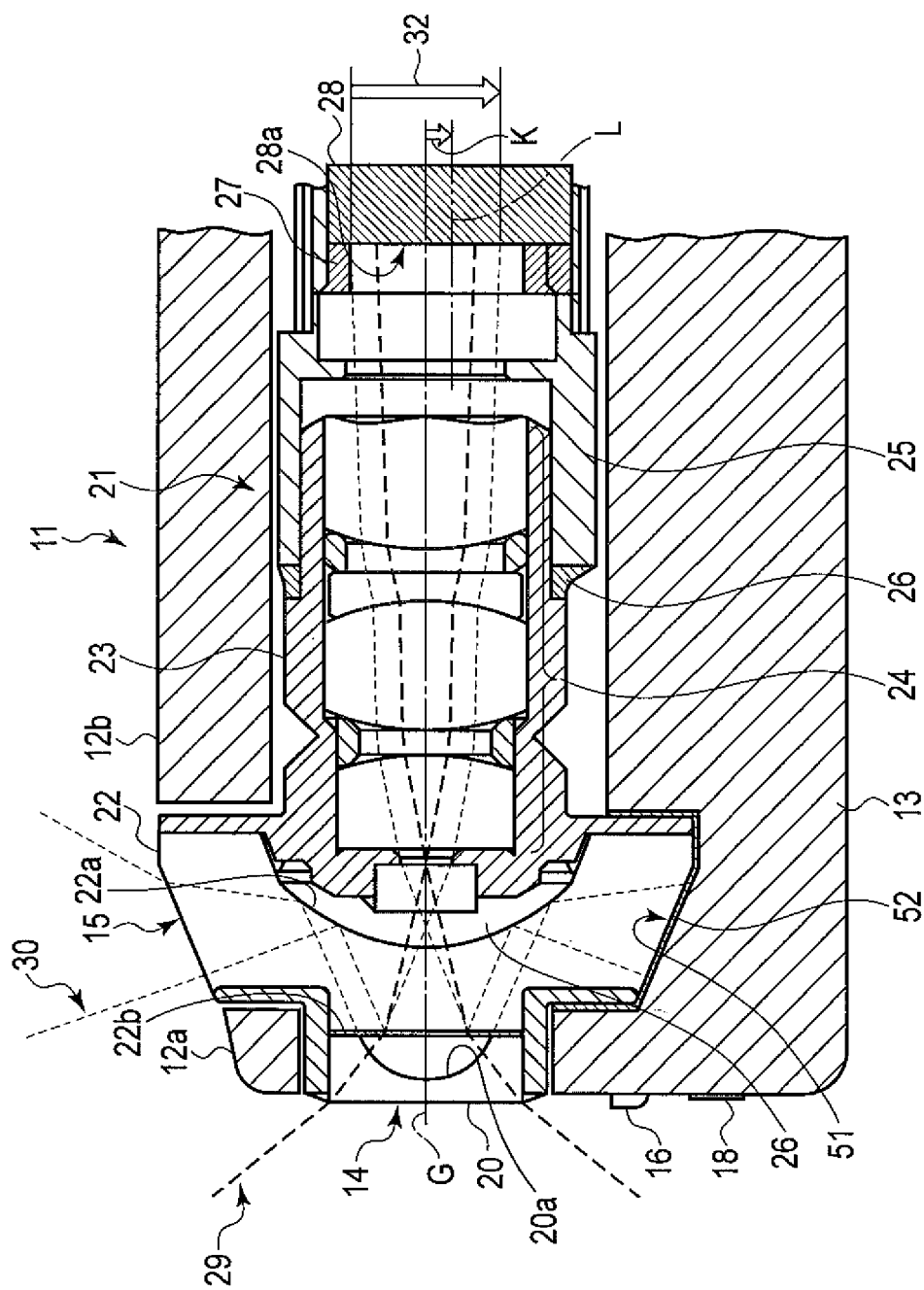
F I G. 5

ENDOSCOPE APPARATUS

CROSS-REFERENCE TO RELATED APPLICATIONS

This is a Continuation Application of PCT Application No. PCT/JP2013/082735, filed Dec. 5, 2013, which was published under PCT Article 21 (2) in Japanese.

This application is based upon and claims the benefit of priority from prior the Japanese Patent Application No. 2012-266358, filed Dec. 5, 2012 the entire contents of which are incorporated herein by references.

BACKGROUND OF THE INVENTION

1. Field of the Invention

The present invention relates to an endoscope apparatus that displays on the same screen a front observation image taken in from a front-viewing observation window in a distal end surface at a distal end portion of an inserting section and a side observation image taken in from a side-viewing observation window on a periphery of a side surface of the distal end portion.

2. Description of the Related Art

In a generally used endoscope apparatus, a front-viewing observation window through which an inserting direction (an axial direction) is imaged in a predetermined viewing region, an illumination window through which illumination light for observation is applied, a forceps hole through which a forceps or the like is extended, and others are arranged on a distal end surface of an inserting section. An imaging lens group (an imaging optical system) and an imaging element are arranged behind this front-viewing observation window, and the imaging element photo-electrically converts an observation light image formed by the imaging lens group to generate a video signal and displays it as a front observation image on, e.g., a monitor.

Further, for example, in Japanese Patent No. 4955838 is suggested an endoscope apparatus having a side-viewing observation window formed of a cylindrical optical element that takes in a side observation target on a lateral periphery orthogonal to the axial direction (the inserting direction) mounted therein in addition to a front-viewing observation window. For example, observation using a colonoscope apparatus involves the possibility that oversight might occur unless observation is carefully performed while rotating a bending section since the colon as an observation target has many rugae. Thus, mounting the side-viewing observation window expands an angle of a viewing field region, thereby further avoiding the oversight.

The front-viewing observation window and the side-viewing observation window are observation windows provided in one optical lens, and observation light images taken in from the respective observation windows are simultaneously formed by using the same optical system and sectioned and projected onto the same light receiving surface of the imaging element. Thus, a front observation image taken in from the front-viewing observation window and a side observation image taken in from the side-viewing observation window are sectioned and enter the same light receiving surface, and a combined observation image is generated by photoelectrical conversion and displayed on a monitor.

In the same monitor display screen, since a screen of a combined image of a front observation image and a side observation image has a smaller display region (a screen size) of the front observation image than a regular screen (the front observation image alone), observation properties are deteriorated with respect to an operator. Further, an operator or a manipulator may experience a strange sensation of perspective or depth, thus requiring reviewing the image.

It is, therefore, an object of the present invention to provide an endoscope apparatus that provides a sufficient display region for a front observation image even in case of a combined image formed of the front observation image and a side observation image and reduces a sensation of strangeness etc., without deteriorating observation properties.

BRIEF SUMMARY OF THE INVENTION

According to an embodiment of the present invention, there is provided an endoscope apparatus comprising: a first observation optical system which is arranged in an inserting section inserted into a lumen and configured to observe an observation target region in a first direction; a second observation optical system which is arranged in the inserting section and includes an annular shape configured to observe an observation target region in the second direction different from the first direction; a support member which supports the first observation optical system and the second observation optical system to have the same optical axis; a pedestal which shields an angular region at part of the second observation optical system against light and is connected to the support member; an imaging section which acquires a combined image of a first observation image based on the observation target region in the first direction, a second observation image based on the observation target region in the second direction, and an image of a non-image-forming region where no image is formed due to the pedestal; a frame which holds the imaging section and the respective observation optical systems so that the imaging section is optically offset with respect to the optical axis of the respective observation optical systems in a direction extending toward the center of the light-shielded angular region; and an imaging optical system which magnifies the combined image to be acquired by the imaging section at a magnification that changes sizes of the second observation image and a boundary portion between the second observation image and the non-image-forming region without disappearing from a light receiving surface of the imaging section and also changes a size of the non-image-forming region so that the non-image-forming region partially remains in a viewing field range but partially protrudes from the viewing field range.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 2A is a view showing an appearance structure of a distal end of an inserting section;

FIG. 2B is a view showing a structure when the distal end of the inserting section is seen from the front;

FIG. 3 is a view showing a sectional structure of a distal end portion of the inserting section including the imaging unit;

FIG. 4A is a view showing an example of a combined image of a front observation image and a side observation image displayed in a monitor according to the first embodiment;

FIG. 4B is a view showing an example of a combined image of a front observation image and a side observation image displayed in a conventional monitor for comparison; and FIG. 5 is a view showing a sectional structure of a distal end portion of an inserting section including an imaging unit according to a modification.

DETAILED DESCRIPTION OF THE PREFERRED EMBODIMENT

Figure 1:
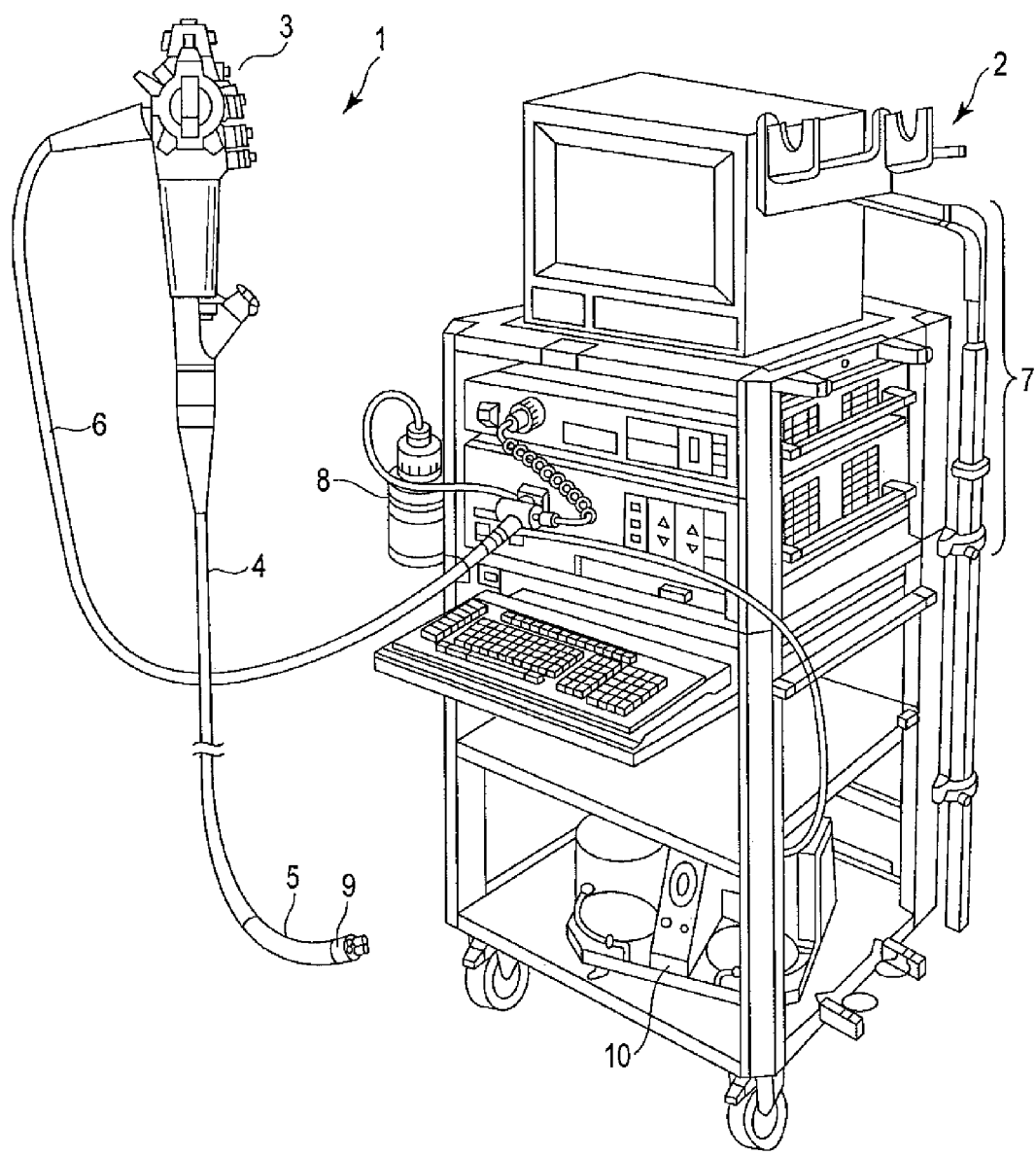
FIG. 1 is a view showing an appearance structure of an endoscope apparatus in which an imaging unit having a front-viewing observation window and a side-viewing observation window is mounted according to a first embodiment.

An embodiment according to the present invention will now be described hereinafter with reference to the drawings.

FIG. 1 is a view showing an appearance structure of an endoscope apparatus in which an imaging unit having a front-viewing observation window and a side-viewing observation window is mounted according to a first embodiment.

The endoscope apparatus according to this embodiment is roughly constituted of an endoscope main body 1 and an endoscope device 7 mounted on a movable trolley 2. This embodiment can be applied to a biological endoscope for observation in a body cavity or a lumen of a biological body or an industrial endoscope for observation in a device such as an engine or a duct. Furthermore, although a flexible scope will be described as an example in this embodiment, the apparatus can be likewise mounted in a rigid scope.

The endoscope main body 1 is constituted of an inserting section (a flexible tube) 4 inserted into a lumen as an observation target, a bending section 5 provided at a distal end thereof, and an operating section 3 that operates the bending section 5 to bend. A distal end portion 9 is provided on a distal end side of the inserting section 4, and a later-described imaging unit is provided in this distal end portion 9. In the following description, the inserting section 4 is determined as the center, and a distal end side extending toward the bending section 5 will be referred to as a distal end side whilst a side extending toward the operating section 3 will be referred to as a proximal end side.

The endoscope device 7 has a light source apparatus that generates illumination light applied to an observation target region, a video processor that performs predetermined image processing to video signals subjected to imaging, a monitor that displays the video signals as an observation image, a keyboard as an input section, and others.

Moreover, a bottle 8 that stores a liquid used for cleaning or the like (a cleaning liquid: e.g., a liquid mainly containing water such as a normal saline solution) is detachably disposed to a support of the trolley 2. Additionally, an air supply pump unit is arranged in the endoscope device V. Further, a suction unit. 10 that sucks a liquid or a gas for cleaning belched into a lumen from later-described cleaning nozzles in the lumen is provided on a rack of the trolley 2.

The endoscope main body 1 is connected to a light source unit with the use of a connector through a universal cable 6. The universal cable 6 includes signal lines through which video signals and others are transmitted and a gas and liquid supply path (a gas supply/liquid supply channel) and a discharge path formed of tubes. The connector connected to the endoscope device 7 side of the universal cable 6 branches for the signal lines, the tube, and a light guide to be connected to respective structural sections.

FIG. 2A is a view showing an appearance structure of the distal end of the inserting section, and FIG. 2B is a view showing a structure when the distal end of the inserting section is seen from the front. FIG. 3 is a view showing a sectional structure of the imaging unit. FIG. 4A shows an example of a combined image of a front observation image and a side observation image displayed in the monitor according to the first embodiment, and FIG. 4B is a view showing an example of a conventional combined image of a front observation image and a side observation image displayed in a monitor for comparison. In a monitor display screen, a vertical direction of the screen is determined as a top-and-bottom direction, and a horizontal direction of the same is determined as a left-and-right direction. In the following description, a traveling direction of the inserting section in a lumen is determined as an inserting direction or an axial direction, a surface seen from the axial direction is determined as the front side (a distal end surface), and a surface orthogonal to the axial direction is referred to as a side surface or a side peripheral surface.

In a distal end portion 9 of the inserting section 4 are provided an imaging unit 11 that protrudes from the distal end surface in the inserting direction (the axial direction) and has a front-viewing observation window 14 and a side-viewing observation window 15 provided thereto, a pedestal 13 that is a distal end structure (a distal end structure region) protruding to have the same height (a frontward projecting height) as the imaging unit 11, a cleaning nozzle 16 arranged near the front-viewing observation window 14 on a front surface of the pedestal 13, cleaning nozzles 17 of the side-viewing observation window 15 arranged on both side surfaces of the pedestal 13, an opening portion 19 of a forceps hole that is opened in the distal end surface and allows a non-illustrated forceps or the like to be inserted therethrough, and an illumination window 18 that is arranged on the front side of the pedestal 13 and allows illumination light for the front-viewing observation window 14 to be applied therefrom.

In the imaging unit 11 are provided the front-viewing observation window 14 through which an observation target that is present on the front side in a lumen is taken in within a predetermined viewing field region and the side-viewing observation window 15 which is arranged behind the front-viewing observation window 14 and through which an observation target present on a peripheral surface in the lumen is taken in within a circumferentially-expanding viewing region. Further, besides the illumination window 18 on the pedestal 18, an illumination window may be arranged on the distal end surface of the inserting section 4, or an illumination window that illuminates the peripheral surface in the lumen may be provided near the side-viewing observation window 15.

The pedestal 13 has a liquid supply path and a gas supply path connected to the cleaning nozzles 16 and 17 arranged therein, and it also has an optical fiber cable arranged therein to lead the illumination light to the illumination window 18 arranged in the front surface. Supposing that the pedestal 13 has a substantially triangular shape, a portion that virtually serves as a base is the same arc surface as a circumferential surface of the distal end portion 9, and portions serving as oblique lines are two side surfaces facing the central side of the front-viewing observation window 14 from both ends of the base. The pedestal 13 substantially has a nearly fan-like shape integrated with the imaging unit 11.

The cleaning nozzles 17 are provided on the two side surfaces of the pedestal 13, respectively. A cleaning liquid belched out from the cleaning nozzles 17 flows in parallel to and comes into contact with a side surface of the side-viewing observation window 15 and further flows to a top portion of the side-viewing observation window 15. Such a liquid flow cleans the side-viewing observation window 15. At the time of cleaning, the cleaning liquid or gas supplied from a supply duct for air supply/liquid supply is belched out from formed nozzle openings toward the observation window 14 and 15, and it is blown to the respective observation windows.

The imaging unit 11 is constituted of an imaging optical system 21 which is a type of optical element and formed of a lens group 24 using lenses and an imaging section 28 formed of an imaging element such as a CCD or a COMS sensor. It is to be noted that the imaging optical system 21 includes a reflection member such as a mirror, a diaphragm member that narrows down a light image, and the like as other optical elements. The lenses are not restricted to those made of glass, and they may be made of any other transparent material, including a resin material.

As shown in FIG. 3, the imaging optical system 21 is configured by combining the lenses (optical elements), and these lenses are aligned and supported in a mirror frame 23 so that optical axes of all the lenses coincide with each other, namely, all the lenses have the same optical axis.

Specifically, the imaging optical system 21 has a concave lens 20 (a first optical element) having a concave surface 20*a* on the proximal end side where the front-viewing observation window 14 arranged at an incidence side distal end is formed and a cylindrical lens (a second optical element) 22 formed into a cylindrical shape (in this embodiment, a conical shape) having a concave surface 22*a* on the proximal end side where the side-viewing observation window 15 arranged behind the concave lens 20 in the optical axis direction is formed.

The cylindrical lens 22 is fitted and fixed in a groove portion 13*a* formed in the pedestal 13. Furthermore, an annular mirror coat member that reflects a light image that has entered from the side-viewing observation window 15 is formed on the concave surface 22*a* of the cylindrical lens 22 on the proximal end side, or it is formed to totally reflect a light image that has entered from the side-viewing observation window 15. An annular mirror coat member 22*b* that again reflects the light image is formed on a flat surface of the cylindrical lens 22 at the distal end thereof. An inner hole in the mirror coat member 22*b* has a function as a diaphragm for the light image that passes through the concave lens 20. The concave lens 20 is appressed against the cylindrical lens 22 to interpose the mirror coat member 22*b* therebetween and fixed by a mirror frame member (a first support member). Here, it is fixed so that optical axes of the concave lens 20 and the cylindrical lens 22 coincide with each other. Besides the exposed mirror frame 23 has an exterior member 12 (12*a* and 12*b*) water-tightly provided except contact with the pedestal 13. A viewing angle of the front-viewing observation window 14 formed by the concave lens 20 is equivalent to a viewing angle of a front-viewing observation window provided in an inserting section of a conventional endoscope apparatus. Furthermore, it is preferable to set an inner viewing angle of the side-viewing observation window 15 to be close to the viewing angle of the front-viewing observation window as much as possible without overlapping. These viewing angles are design factors and are appropriately set according to the observation object.

In addition, to display a demarcation line at a boundary between a front observation image and a side observation image shown in FIG. 4A, forming a linear non-reflective fringe on an annular inner edge of the mirror coat member 22*b* prevents passage and reflection of an observation light image at the fringe portion alone, and hence the boundary can be displayed as the demarcation line.

Moreover, a proximal end side of the cylindrical lens 22 is bonded to a distal end portion (the first support member) of the mirror frame 23, and concave lenses and convex lenses are arranged in the mirror frame 23 along the optical axis direction. An imaging holding frame 25 that holds the imaging section 28 is fitted on the proximal end side of the mirror frame 23 and fixed by, e.g., an adhesive 26. The imaging holding frame 25 holds the periphery of the imaging section 28, and a mask member 27 with a function of an aperture that defines an imaging range is provided on a light receiving surface 28*a* of the imaging section 28.

Formation of a front observation image and a side observation image by the front-viewing observation window 14 and the side-viewing observation window 15 in the imaging optical system 21 will now be described with reference to FIG. 3. It is to be noted that an observation image provided before image formation is called a light image.

A light image that has entered the concave lens 20 of the front-viewing observation window 14 is narrowed down by the mirror coat member 22*b*, enters the cylindrical lens 22 to be converged, and enters the lens group 24 supported by the mirror frame 23 through a space. At this moment, the light image is focused near a lens placed at the distal end of the lens group 24 and crosses the optical axis, and a direction of the light image is reversed (the top-and-bottom and light-and-right directions), thus providing a reversed light image. Then, the reversed light image passes through the lens group 24 and is turned to a front observation image formed in a central circular region of the light receiving surface 28*a* of the imaging section 28.

On the other hand, a light image that has entered from the side surface of the cylindrical lens 22 of the side-viewing observation window 15 is internally reflected on the concave surface 22*a* and travels to a reflection surface of the mirror coat member 22*b*. The light image reflected on this reflection surface passes through the concave surface 22*a* and enters the lens group 24 supported by the mirror frame 23 to be converged through the space. At this moment, the light image is focused at the same position as the front observation image and crosses the optical axis, and a direction of the light image is reversed (the top-and-bottom direction and left-and-right directions), thereby providing a reversed light image. Then, the reflected light image passes through the lens group 24 and turns to a side observation image formed on the light receiving surface 28*a* of the imaging section 28 to annularly surround the central region of the front observation image.

Moreover, as an arrangement relationship between the imaging optical system 21 and the imaging section 28, a center position L of the light receiving surface 28 of the imaging section 28 is generally arranged to overlap an optical axis G of the imaging optical system 21. In this arrangement, as a combined image of a front observation image 42 and a side observation image 43 on the light receiving surface 41 acquired by the imaging section, the whole of both the front observation image 42 and the side observation image 43 is displayed within a light receiving surface as shown in FIG. 4B. Additionally, in regard to the side observation image 43, the pedestal 13 is provided in contact with the imaging unit 11. Thus, part of the pedestal 13 serves as a light shielding section 51, and a non-image-forming region 44 is produced in the side-viewing observation window 15. The non-image-forming region 44 functions as a non-observation viewing field.

In this embodiment, as shown in FIG. 3, the imaging section 28 is arranged to shift toward the pedestal 13 side so that a displacement of a shift distance K can be produced between the optical axis G that is the center of a light image path of the imaging optical system 21 and the center position L of the light receiving surface of the imaging section 28. Although the shift distance K of the imaging section 28 differs depending on a magnification of the imaging optical system and a light receiving area of the imaging element, it is a distance of, e.g., approximately 1 mm or less.

Thus, in FIG. 3, an observation target image 32 formed on the light receiving surface 28a shifts upward with respect to the center position L of the light receiving surface 28a. That is, the observation target image 32 to be displayed shifts downward so that the non-image-forming region 44 is incomplete on the light receiving surface 41 as shown in FIG. 4(a). Since the observation image is not taken in, this non-image-forming region 44 does not have to be displayed in the monitor for an operator, and no trouble occurs even if this non-image-forming region 44 is intentionally formed to be incomplete.

Thus, in this embodiment, as described above, the imaging section 28 is moved to shift the center position L of the light receiving surface with respect to the optical axis G, a magnification of the imaging optical system is adjusted to magnify and display a combined image of the front observation image 42 and the side observation image 43, the non-image-forming region 44 is protruded to the outside of the display screen, and the imaging optical system is magnified and adjusted until a viewing field range (a display range) of the side observation image reaches corners of the top and the bottom of the light receiving surface 41. This magnifying adjustment is performed by changing/adjusting a lens magnification of the imaging optical system 21 and set so that boundary portions 43a between the side observation image 43 and the non-image-forming region 44 can be prevented from disappearing. It is to be noted that, when a combined image of a front observation image and a side observation image in the prior art shown in FIG. 4B is simply magnified and displayed, the front observation image is magnified, but the side observation image protrudes from the display screen, and part of the side observation image (an image in the top-and-down direction in particular) disappears without being displayed, thereby obstructing observation.

The configuration in which the light receiving surface of the imaging section moves with respect to the optical axis has been described but, on the contrary, the imaging optical system may be moved with respect to the center of the imaging element so that the optical axis is shifted.

The shift distance K at the position where the viewing field of the side observation image 43 is complete in this situation is as follows:

$$K = \alpha/2 \times (1-\cos\theta)/(1+\cos\theta) \quad (1)$$

where α is a height of the light receiving surface 41 of the imaging element in a direction parallel to a shifting direction, K is the shift distance, and θ is a spread angle seen from the optical axis of the non-image-forming region 44 with respect to the top-and-bottom direction (a perpendicular line). Further, assuming that R is a longer one of distances between the optical axis G and the top and bottom corners of the light receiving surface 41 as the viewing field range, R is as follows:

$$R = \alpha/(1+\cos\theta) \quad (2)$$

As described above, the imaging unit 11 that acquires the combined image of the front observation image 42 and the side observation image 43 offsets the optical axis of the imaging optical system 21 and the center of the light receiving surface of the imaging section (the imaging element) toward the non-image-forming region 44 by shifting. A light image of the non-image-forming region 44 formed on the light receiving surface of the imaging section is eliminated from the monitor screen, minimized, and displayed, and substantial display regions of observation images are increased. Thus, the display region of the front observation image 42 can be increased without affecting the display region of the side observation image 43.

Furthermore, in the case of realizing the same by trimming processing for eliminating the non-image-forming region 44 and magnification display processing for combined images, these processes reduce the number of pixels (CCD pixels) substantially used by the imaging element, quality of images that should be improved is deteriorated, and even fine parts must be observed so that overlooking can be prevented. Thus, realization using the moving image processing based on software is possible, but the imaging element and an image processing circuit (e.g., CPU) must be improved in terms of performance, thereby leading to an increase in cost.

On the other hand, adopting hardware using a process of shifting the optical axis and the light receiving surface center position and a process of adjusting the imaging optical system requires changing characteristics of the imaging optical system from those in the prior art at the time of design, but improvement in the performance of the imaging element or substantial image processing can be realized at minimum cost.

A modification of this embodiment will now be described.

FIG. 5 is a view showing a sectional structure of a distal end portion of an inserting section including an imaging unit according to the modification. The structure of the distal end of the inserting section according to this modification is equal to the structure of the first embodiment except for a mounting structure of an imaging unit 11, and the same reference numerals are given to omit a description.

A cylindrical lens 22 of the imaging unit 11 is fitted and supported in a groove portion 13a provided in a pedestal 13. In this modification, a buffer member 52 is inserted to reach a side-viewing observation window 15 and a mirror frame 23 of the cylindrical lens 22 between the cylindrical lens 22 and the groove portion (a light shielding section 51) 13a. This buffer member 52 is provided to interpose an elastic adhesive, e.g., a silicone-based elastic adhesive or a rubber sheet.

According to this modification, interposing the buffer member 52 between the cylindrical lens 22 and the groove portion (the light shielding section) 13a can buffer an impact shock to prevent damage when the impact shock is given to the cylindrical lens 22 from the outside. The impact shock from the outside often occurs during conveyance or attachment/detachment to/from a cleaner or the like rather than during use for observation.

Furthermore, when the buffer member 52 is made of a material that prevents penetration of a liquid and the cylindrical lens 22 and the groove portion (the light shielding section) 13a are provided to be appressed against each other, a watertight function of preventing water or the like from entering the inserting section can be provided.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope apparatus comprising:
   a first observation optical system which is arranged in an inserting section inserted into a lumen and configured to observe an observation target region in a first direction;
   a second observation optical system which is arranged in the inserting section and includes an annular shape configured to observe an observation target region in a second direction different from the first direction;
   a support member which supports the first observation optical system and the second observation optical system to have an optical axis that is the same;
   a pedestal which shields an angular region at part of the second observation optical system against light and is connected to the support member;
   an imaging section which acquires a combined image of (i) a first observation image based on the observation target region in the first direction, (ii) a second observation image based on the observation target region in the second direction, and (iii) an image of a non-image-forming region that provides a non-observation viewing field due to the pedestal;
   a frame which holds the imaging section and the respective observation optical systems so that a center of the imaging section is optically offset with respect to the optical axis of the respective observation optical systems in a direction extending toward a center of the light-shielded angular region; and
   an imaging optical system which magnifies the combined image at a magnification where part of the image on a circumference side of the non-image-forming region disappears and the second observation image readies both ends of a top and bottom of a light receiving surface of the imaging section without disappearing, by the offset.

2. The apparatus according to claim 1,
   wherein the imaging optical system magnifies the combined image to be acquired by the imaging section at a magnification that enables the viewing field range of the second observation image to reach edges of a top and a bottom of the light receiving surface of the imaging section.

3. The apparatus according to claim 1, further comprising a distal end structure region which comprises the pedestal and is integrally arranged on a distal end surface of the inserting section at the same protruding height as the first observation optical system,
   a portion of the distal end structure region connected to the support member shielding the angular region forming a partially annular shape against light with respect to the second observation optical system.

4. The apparatus according to claim 3,
   wherein, in the distal end structure region:
   an illumination window is arranged near the first observation optical system provided on a first direction side, and
   nozzles from which a liquid for cleaning is belched out toward the first and second observation optical systems are arranged in the first and second directions, and a duct through which the liquid is supplied to the nozzles is internally provided in the distal end structure region.

5. The apparatus according to claim 3,
   wherein an offset distance K is represented by the following expression:

$K=\alpha/2 \times (1-\cos\theta)/(1+\cos\theta)$ where K is a distance from the optical axis in the imaging optical system to the center on the offset light receiving surface, α is a height of the light receiving surface of the imaging section, and θ is a spread angle between a center and an end portion of the angular region having a partially annular shape light-shielded by the distal end structure region.

6. The apparatus according to claim 3,
   wherein, in a state that the second observation image does not disappear from the light receiving surface of the imaging section and a boundary between the second observation image and the light-shielded angular region remains within the light receiving surface, the following expression is achieved:

$R=\alpha/(1+\cos\theta)$ where α is a height of the light receiving surface in a direction parallel to a direction of the offsetting,
   R is a longer one of distances between the optical axis of the first observation optical system and the second observation optical system and corners of a top and a bottom of the light receiving surface in the direction parallel to the direction of the offsetting, and
   θ is a spread angle between the center and an end portion of the angular region having the partially annular shape light-shielded by the distal end structure region when viewed from the optical axis.

* * * * *